US012582541B2

(12) United States Patent
Riordan

(10) Patent No.: US 12,582,541 B2
(45) Date of Patent: Mar. 24, 2026

(54) CRYOTHERAPY AND COMPRESSION SLEEVE AND METHODS OF USE

(71) Applicant: FREEZE SLEEVE IPCO LLC, Mt. Kisco, NY (US)

(72) Inventor: Michael Riordan, Alpharetta, GA (US)

(73) Assignee: FREEZE SLEEVE IPCO LLC, Mt. Kisco, NY (US)

( * ) Notice: Subject to any disclaimer, the term of this patent is extended or adjusted under 35 U.S.C. 154(b) by 1148 days.

(21) Appl. No.: 15/224,526

(22) Filed: Jul. 30, 2016

(65) Prior Publication Data

US 2017/0027734 A1 Feb. 2, 2017

Related U.S. Application Data

(60) Provisional application No. 62/199,623, filed on Jul. 31, 2015.

(51) Int. Cl.
A61F 5/01 (2006.01)
A61F 7/00 (2006.01)
(Continued)

(52) U.S. Cl.
CPC .............. A61F 5/0109 (2013.01); A61F 7/02 (2013.01); A61F 7/10 (2013.01);
(Continued)

(58) Field of Classification Search
CPC .... A61F 5/0104; A61F 5/0106; A61F 5/0109; A61F 5/0111; A61F 5/0118; A61F 7/10;
(Continued)

(56) References Cited

U.S. PATENT DOCUMENTS

| | | | | |
|---|---|---|---|---|
| 1,487,453 | A | * | 3/1924 | Fournier .................. A41B 7/00 |
| | | | | 2/124 |
| 3,892,239 | A | * | 7/1975 | Masso Remiro ....... A61F 13/06 |
| | | | | 604/312 |

(Continued)

FOREIGN PATENT DOCUMENTS

| | | |
|---|---|---|
| JP | S63237938 A | 10/1988 |
| JP | 2001513394 A | 9/2001 |

(Continued)

OTHER PUBLICATIONS

WikiDiff. "Fasten vs Tighten". https://wikidiff.com/tighten/fasten. (Year: 2017).*

(Continued)

*Primary Examiner* — Ophelia A Hawthorne
(74) *Attorney, Agent, or Firm* — THOMPSON HINE LLP

(57) ABSTRACT

An elastic material or other stretch material formed as a layer or cylinder and capable of holding hot or cold temperature and radiating such temperature through contact and an elastic fabric adhered to the elastic material capable of providing a protective cover and a fabric liner between a user's skin and the elastic material and, thus, functions to conform to user's body providing evenly distributed encompassing cold or hot temperature application, a fabric liner between user's skin and the hot or cold therapy, even application of compression therapy without the need for clips or buckles.

27 Claims, 6 Drawing Sheets

(51) Int. Cl.
  *A61F 7/02*     (2006.01)
  *A61F 7/10*     (2006.01)
(52) U.S. Cl.
  CPC ................. *A61F 2007/0029* (2013.01); *A61F 2007/0031* (2013.01); *A61F 2007/0032* (2013.01); *A61F 2007/0034* (2013.01); *A61F 2007/0039* (2013.01); *A61F 2007/0041* (2013.01); *A61F 2007/0042* (2013.01); *A61F 2007/0043* (2013.01); *A61F 2007/0219* (2013.01); *A61F 2007/0223* (2013.01); *A61F 2007/0233* (2013.01); *A61F 2007/0244* (2013.01)
(58) Field of Classification Search
  CPC ................. A61F 7/02; A61F 2007/0233; A61F 2007/0223; A61F 2007/0034; A61F 2007/0041; A61F 2007/0043; A61F 2007/0032; A61F 2007/0029; A61F 2007/0031; A61F 2007/0039; A61F 2007/0244; A61F 2007/0219; A61F 2007/0042
  USPC .......................................................... 602/2
  See application file for complete search history.

(56)                References Cited

U.S. PATENT DOCUMENTS

| | | | | |
|---|---|---|---|---|
| 4,084,586 A * | 4/1978 | Hettick ................. | A61F 5/0118 |
| | | | | 602/60 |
| 4,534,354 A | 8/1985 | Bonner, Jr. et al. | |
| 4,671,267 A | 6/1987 | Stout | |
| 4,961,418 A | 10/1990 | McLaurin-Smith | |
| 5,080,089 A * | 1/1992 | Mason ..................... | A61F 7/00 |
| | | | | 607/104 |
| 5,172,689 A | 12/1992 | Wright | |
| 7,060,086 B2 | 6/2006 | Wilson et al. | |
| 7,621,944 B2 | 11/2009 | Wilson et al. | |
| 8,336,122 B1 * | 12/2012 | Harris ................... | A42B 3/122 |
| | | | | 29/458 |
| 2003/0083605 A1 | 5/2003 | Edmund | |
| 2003/0109910 A1 | 6/2003 | Lachenbruch et al. | |
| 2003/0135171 A1 | 7/2003 | Ingram et al. | |
| 2005/0124925 A1 | 6/2005 | Scherpenborg | |
| 2006/0004427 A1 | 1/2006 | Wilson et al. | |
| 2010/0298915 A1 | 11/2010 | Whitely | |
| 2011/0098792 A1 | 4/2011 | Lowe et al. | |
| 2014/0276253 A1 * | 9/2014 | Varga ................... | A61H 9/0078 |
| | | | | 601/15 |
| 2014/0276258 A1 * | 9/2014 | Hall ..................... | A61N 1/0456 |
| | | | | 601/18 |

FOREIGN PATENT DOCUMENTS

| | | |
|---|---|---|
| JP | 2003290270 A | 10/2003 |
| JP | 2006255347 A | 9/2006 |
| WO | 9712570 A1 | 4/1997 |
| WO | 2007026504 A1 | 3/2007 |

OTHER PUBLICATIONS

International Search Authority, "International Search Report and Written Opinion," PCT/US16/44930, mailed Oct. 17, 2016.

* cited by examiner

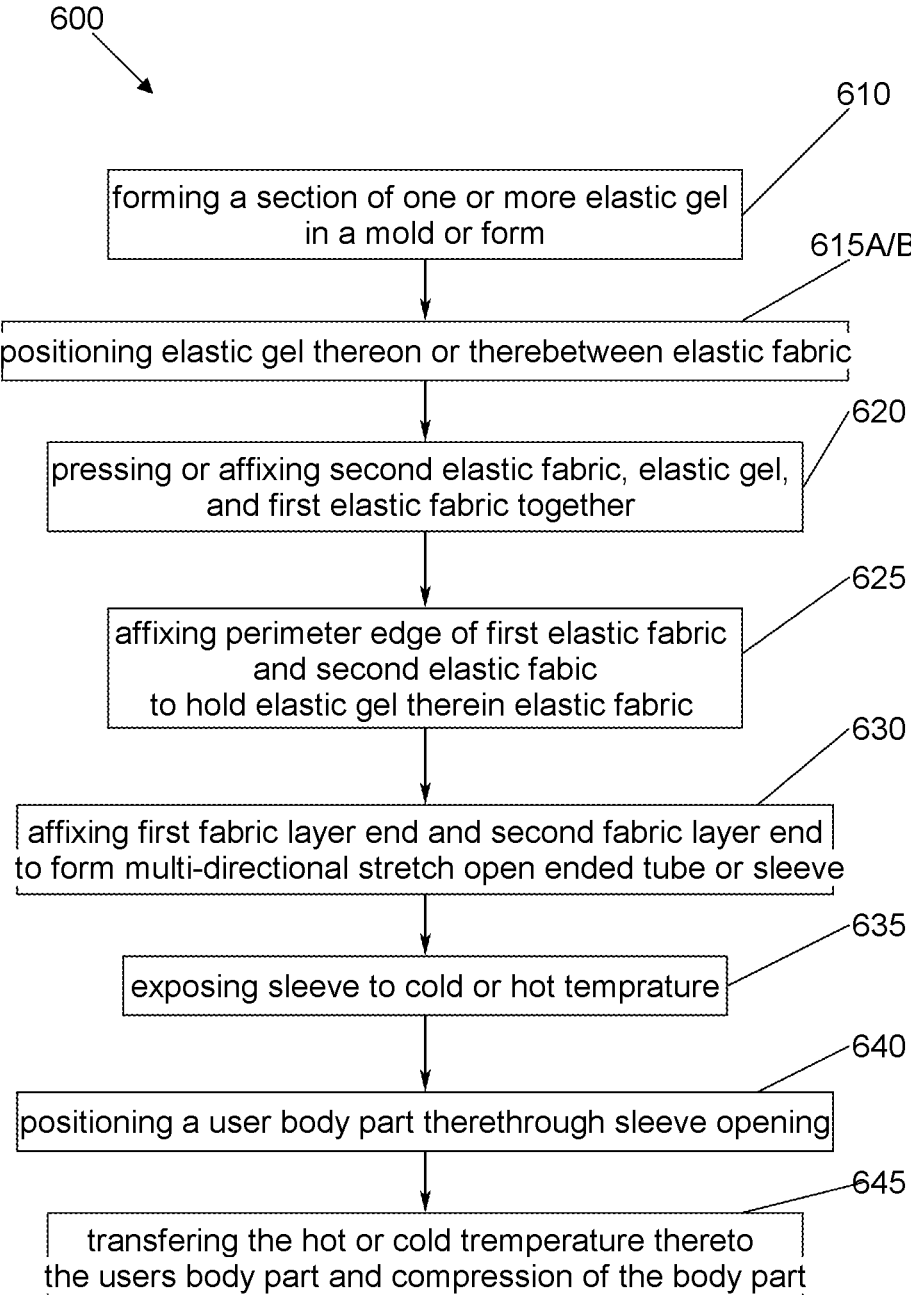

600

610 forming a section of one or more elastic gel
in a mold or form

615A/B positioning elastic gel thereon or therebetween elastic fabric

620 pressing or affixing second elastic fabric, elastic gel,
and first elastic fabric together

625 affixing perimeter edge of first elastic fabric
and second elastic fabic
to hold elastic gel therein elastic fabric

630 affixing first fabric layer end and second fabric layer end
to form multi-directional stretch open ended tube or sleeve

635 exposing sleeve to cold or hot temprature

640 positioning a user body part therethrough sleeve opening

645 transfering the hot or cold tremperature thereto
the users body part and compression of the body part

FIG. 6

CRYOTHERAPY AND COMPRESSION SLEEVE AND METHODS OF USE

CROSS-REFERENCE TO RELATED APPLICATIONS

To the full extent permitted by law, the present United States Non-provisional patent application hereby claims priority to and the full benefit of, United States Provisional Application entitled "A combined cryotherapy and compression sleeve free from all fastening devices and removeable gel-packs to treat sore muscles and/or joints," having assigned Ser. No. 62/199,623, filed on Jul. 31, 2015, which is incorporated herein by reference in its entirety.

FEDERALLY SPONSORED RESEARCH OR DEVELOPMENT

None

PARTIES TO A JOINT RESEARCH AGREEMENT

None

REFERENCE TO A SEQUENCE LISTING

None

TECHNICAL FIELD

The disclosure generally relates to a limb or body part cover. More specifically, the instant disclosure relates to a cold and compression therapy apparatus with a combined cryotherapy and compression for treatment of a sprained, strained, or bruised body part.

BACKGROUND

Muscle and joint injuries are common in life, sports, and exercise. As soon as possible after an injury, such as an elbow, knee or ankle sprain, you can relieve the pain and swelling and promote healing with rest, ice, compression, and elevation. Specifically, ice will reduce pain and swelling, and compression or wrapping the injured or sore area with an elastic bandage (such as an Ace wrap), will help decrease swelling.

Inflammation is a localized physical condition in which part of the body becomes reddened, swollen, hot, and often painful, especially as a reaction to injury. One approach is the concept of icing or application of ice (cryotherapy) to the skin above an area of a ligament sprain, muscle strain, bruise or the like. Ice is also often helpful with chronic overuse or tissue fatigue injuries such as carpal tunnel syndrome, tennis elbow, supraspinatus tendinitis, iliotibial band syndrome, patellofemoral pain syndrome, shin splints, plantar fasciitis, or tendinitis, especially joints healing from repetitive injury. One disadvantage with this approach is ice is wet and slippery especially once it begins to melt making it difficult to hold in place on the area of the injury. Moreover, ice is rigid, non-conforming, and fluctuates in temperature being too cold at first and then not cold enough once the ice partially melts leaving insulating water between the injury and the ice. Furthermore, ice should not be applied directly to the skin rather a towel or other fabric liner should be placed between the skin and the ice.

Another approach is the concept of compression therapy or application of compression to an injured area such as, one of the injuries listed above. Compression is a simple and efficient mechanical principle, the application of an elastic band, around the area of a ligament sprain, muscle strain, bruise or the like to stabilize the injury and decrease swelling. One disadvantage with this approach is wrapping the elastic band too tightly resulting in more swelling in the injured area. Moreover, this approach requires external fasteners, such as clips or buckles to hold the elastic band in place. Furthermore, this approach of wrapping an elastic band around a joint, such as an elbow, knee, ankle or shoulder, loosens its grip during joint use or movement.

Therefore, it is readily apparent that there is a recognized unmet need for a cryotherapy and compression sleeve and methods of use that designed to address at least some aspects of the problems discussed above.

BRIEF SUMMARY

Briefly described, in example embodiment, the present apparatus overcomes the above-mentioned disadvantage, and meets the recognized need for a cryotherapy and compression sleeve and methods of use including, in general, an elastic material or other stretch material formed as a layer or cylinder and capable of holding hot or cold temperature and radiating such temperature through contact and an elastic fabric adhered to the elastic material capable of providing a protective cover and a fabric liner between a user's skin and the elastic material and, thus, functions to conform to user's body providing evenly distributed encompassing cold or hot temperature application, a fabric liner between user's skin and the hot or cold therapy, even application of compression therapy without the need for clips or buckles.

In an exemplary embodiment, an apparatus for wrapping a body part, the apparatus including an elastic material formed as a layer and having a first surface and a second surface, the elastic material configured for hot or cold temperature transfer and compression thereof the body part, and an elastic fabric adhered to the first surface and the second surface of the elastic material, the elastic fabric configured to provide a protective cover for the first surface and a liner for the second surface.

In still a further exemplary embodiment of a method of utilizing a hot or cold temperature transfer and compression sleeve to wrap a user's body part therein, the method including the steps of forming an elastic material in a mold and having a first surface and a second surface, the elastic material configured for hot or cold temperature transfer and compression thereof the body part, positioning the elastic material thereon an elastic fabric having a first elastic fabric and a second elastic fabric, the first elastic fabric adhered to the first surface and the second elastic fabric adhered to the second surface of the elastic material, the elastic fabric configured to provide a protective cover for the first surface and a liner for the second surface, pressing the elastic fabric thereto the elastic material, sealing first elastic fabric thereto the second elastic fabric to hold the elastic material therein, affixing a first fabric edge of the first elastic fabric thereto a second fabric edge of the second elastic fabric to form an open ended tub.

Accordingly, a feature of the cryotherapy and compression sleeve and methods of use is the ability to utilize elastic material or other compatible hot/cold multi-directional stretch material formed as a layer, cylinder, or other shape and configured to encompass a body part or section of a limb, such as an ankle, knee, wrist, elbow, or other body part.

Another feature of the cryotherapy and compression sleeve and methods of use is the ability to utilize elastic fabric or other compatible multi-directional stretch fabric and configured to provide an outer protective cover for the elastic material and an internal fabric liner for the elastic material to act as a transition barrier between a user's skin and the elastic material.

Still another feature of the cryotherapy and compression sleeve and methods of use is its ability to be formed cylindrically or tube shaped, or with or without a tapper from one end to the other and having openings on each end.

Yet another feature of the cryotherapy and compression sleeve and methods of use is its ability to fully encompass or surround the targeted area, such as a body part or section of a limb, such as an ankle, knee, wrist, elbow, or other body part, and maintain its fit and placement.

Yet another feature of the cryotherapy and compression sleeve and methods of use is its ability to enable one hand installation thereon a user's targeted area, such as a body part or section of a limb, such as an ankle, knee, wrist, elbow, or other body part without the use of pins, fasteners, ties, wraps, clasps, or other fasteners.

Yet another feature of the cryotherapy and compression sleeve and methods of use is its ability to store in a flat configuration and may be stacked, rolled, or folded taking up a small space, especially when cooling in a freezer.

Yet another feature of the cryotherapy and compression sleeve and methods of use is its ability to maintain its soft and flexible form at all times whether hot, warm, cool or cold.

Yet another feature of the cryotherapy and compression sleeve and methods of use is its ability to be heated and cooled without losing its shape.

Yet another feature of the cryotherapy and compression sleeve and methods of use is to provide an elastic material completely encapsulated by the elastic fabric.

Yet another feature of the cryotherapy and compression sleeve and methods of use is to provide an integral elastic material encapsulated by the elastic fabric enabling the sleeve to be heated or cooled together.

Yet another feature of the cryotherapy and compression sleeve and methods of use is to provide an integral elastic material encapsulated by the elastic fabric having an integral fabric liner positioned between the skin and the cold source.

Yet another feature of the cryotherapy and compression sleeve and methods of use is it provides a non-condensation forming integral elastic material encapsulated by the elastic fabric sleeve different from ice, ice packs, or gel packs making it difficult to hold ice, ice packs, or gel packs in place on the area of the injury.

Yet another feature of the cryotherapy and compression sleeve and methods of use is it provides a flexible conforming integral elastic material encapsulated by the elastic fabric sleeve.

Yet another feature of the cryotherapy and compression sleeve and methods of use is it provides a more constant temperature apparatus formed of elastic material verses large fluctuations in temperature being too cold at first and then not cold enough once the ice or ice packs begin to melt.

Yet another feature of the cryotherapy and compression sleeve and methods of use is it provides a flexible conforming integral elastic material encapsulated by the elastic fabric sleeve in various sizes to prevent an overly tight fit resulting in more swelling in the injured area.

Yet another feature of the cryotherapy and compression sleeve and methods of use is it provides a flexible conforming integral elastic material encapsulated by the elastic fabric sleeve that requires no external fasteners, such as clips or buckles to hold the elastic band in place.

Yet another feature of the cryotherapy and compression sleeve and methods of use is it provides a flexible conforming integral elastic material encapsulated by the elastic fabric sleeve that does not loosen around a joint, such as an elbow, knee, ankle or shoulder, nor loosens its grip during joint use or movement.

Yet another feature of the cryotherapy and compression sleeve and methods of use is its safe, simple, inexpensive, and easy to self-apply.

Yet another feature of the cryotherapy and compression sleeve and methods of use is it enables both cold and compression with quick and easy application after activity to reduce pain, muscle spasm, inflammation, and blood flow or swelling to the affected area.

Yet another feature of the cryotherapy and compression sleeve and methods of use is it enables both cold and compression to reduce the release of chemicals that cause pain and inflammation.

These and other features of the cryotherapy and compression sleeve and methods of use will become more apparent to one skilled in the art from the following Detailed Description of the Embodiments and Claims when read in light of the accompanying drawing Figures.

BRIEF DESCRIPTION OF THE DRAWINGS

The present cryotherapy and compression sleeve and methods will be better understood by reading the Detailed Description of the embodiments with reference to the accompanying drawing figures, in which like reference numerals denote similar structure and refer to like elements throughout, and in which:

FIG. 6 is a flow diagram of the steps to form the integral elastic material being affixed to the elastic fabric of cryotherapy and compression sleeve shown in FIG. 1.

It is to be noted that the drawings presented are intended solely for the purpose of illustration and that they are, therefore, neither desired nor intended to limit the disclosure to any or all of the exact details of construction shown, except insofar as they may be deemed essential to the claimed invention.

DETAILED DESCRIPTION

In describing the exemplary embodiments of the present disclosure, as illustrated in FIGS. 1-6 specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples, and are merely examples among other possible examples.

Figure 1:
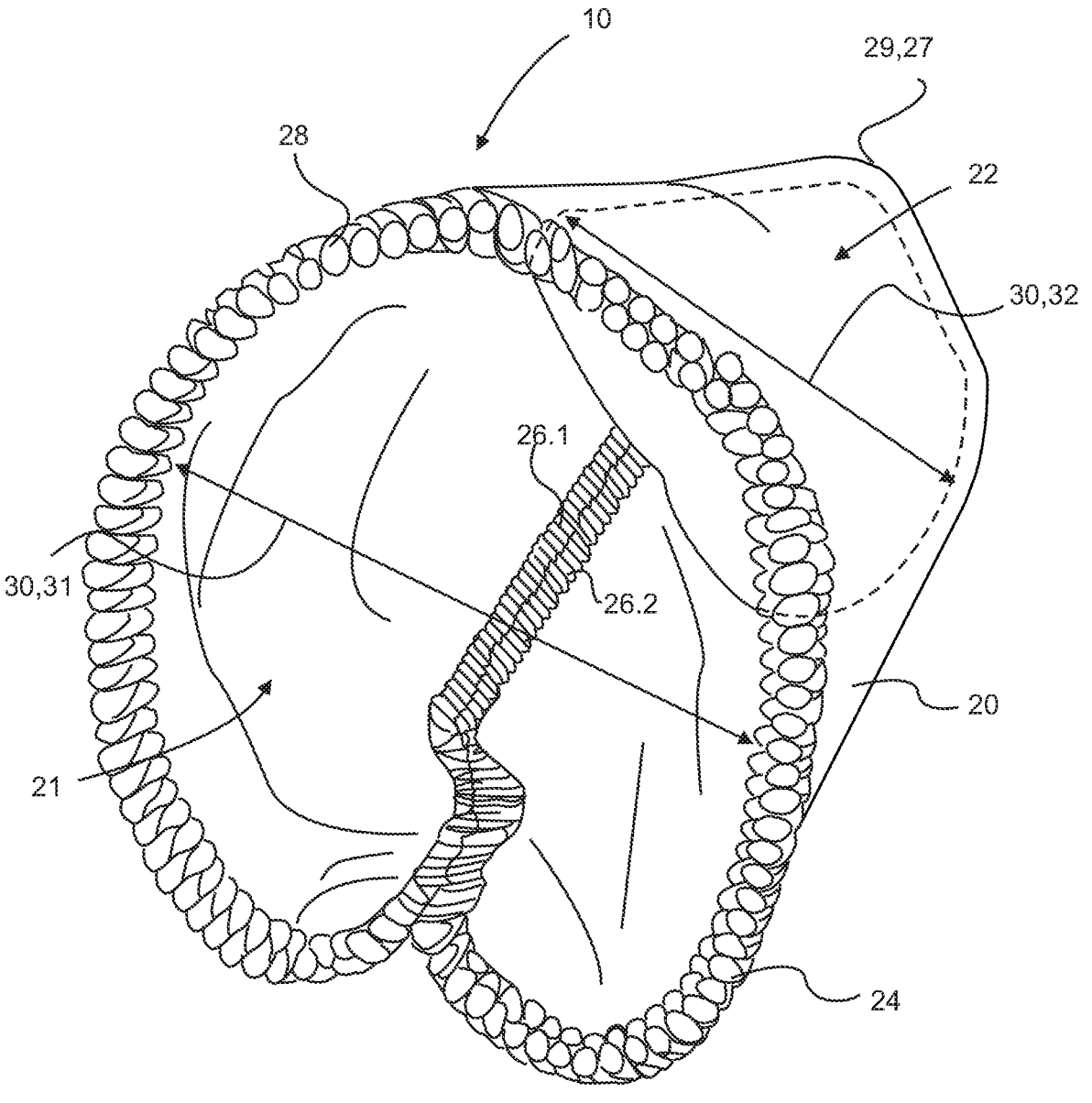
FIG. 1 is a side perspective view of an exemplary embodiment of the cryotherapy and compression sleeve.

Referring now to FIG. 1 there is illustrated an exemplary embodiment of cryotherapy and compression sleeve 10. Cryotherapy and compression sleeve 10 may include sleeve body 20 wherein sleeve body 20 may be configured or shaped in the form of a tube or cylindrical shaped or open ended tubular sleeve. It is contemplated herein that sleeve body 20 may be shaped in the form of a tube or cylinder or formed in a planar shape and rolled into a tube or cylinder. Moreover, sleeve body 20 may include one or more openings or apertures, such as first sleeve opening 21 and second sleeve opening 22. It is further contemplated herein that sleeve body 20 may be tapered between first sleeve opening 21 and second sleeve opening 22. As such first sleeve opening 21 may be configured having a larger radius (greater than) or sleeve opening diameter 30, such as first sleeve opening diameter 31 is greater than and tapper thereto (in diameter) second sleeve opening diameter 32, or vice-a-versa. Furthermore, cryotherapy and compression sleeve 10 or sleeve body 20 may include one or more edges, such as first sleeve edge 28 and second sleeve edge 29, which run or traverse the circumference of first sleeve opening 21 and second sleeve opening 22 of sleeve body 20 and/or first sleeve linear edge 26.1 and second sleeve linear edge 26.2, which run or traverse the length of sleeve body 20. Either of first sleeve edge 28 and second sleeve edge 29 may include folded sleeve edge 27 or seamed sleeve edge 24. First sleeve linear edge 26.1, second sleeve linear edge 26.2, and/or first sleeve edge 28 may be sealed (seal), affixed, such as by sewn together via single or multiple stitch, hemmed, glued, ties, braids, heated, heat pressed, stapled, snapped, hook and loop, taped, or otherwise attached to configure or shape cryotherapy and compression sleeve 10 or sleeve body 20 in the form of a tube or cylinder.

In use, for example, when sliding a user's hand through first sleeve opening 21 and second sleeve opening 22, and pulling or sliding cryotherapy and compression sleeve 10 up to the user's bicep muscle to position sleeve body 20 around the user's elbow, then larger opening first sleeve opening 21 grips user's bicep and smaller opening second sleeve opening 22 grips user's forearm. Similar uses are recognized for user's wrist, forearm, knee, ankle and other body parts.

Figure 2:
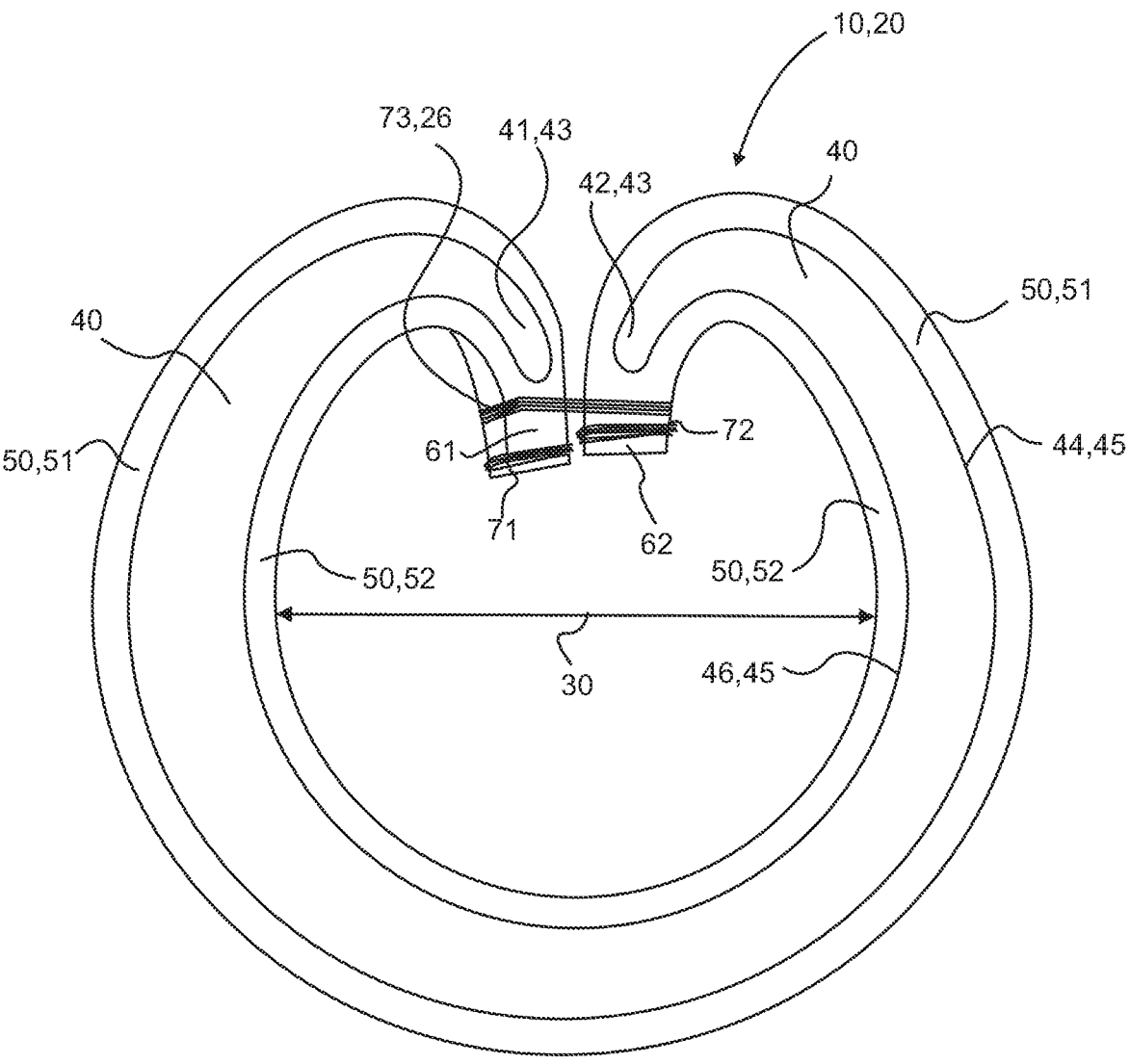
FIG. 2 is a cross-sectional view of cryotherapy and compression sleeve shown in FIG. 1.

Referring now to FIG. 2 there is illustrated an exemplary embodiment of a cross sectional view of a common section of cryotherapy and compression sleeve 10. Cryotherapy and compression sleeve 10 or sleeve body 20 may include flexible hot or cold transfer material or gel, such as elastic material 40, or other stretchable material capable of being shaped as a layer, tube, cylinder, bent, or otherwise and capable of holding hot or cold temperature and radiating such temperature change or transfer through contact. It is contemplated herein that elastic material 40 may be shaped in the form of a tube or cylinder or bent as in a 90 degrees or any other acute angle, or formed in a planar shape and rolled into a tube or cylinder having diameter 30. In one embodiment, elastic material 40 may be formed in a planar shape having perimeter edge 43 or one or more material sides, such as first material side 41 and second material side 42. Moreover, elastic material 40 may be configured having one or more surfaces 45, such as first material surface 44 and second material surface 46.

Elastic material 40 is preferably formed from a hot/cold absorption and transfer capability material (heat transfer) and/or multi-directional stretch elastic material or constructed of other suitable materials such as polymer, gel or the like, that can be utilized, provided such material has sufficient hot/cold absorption and transfer capability and/or multi-directional stretch elastic material capable of being formed as a layer, cylinder, or other shape to encompass a body part or section of a limb, such as an ankle, knee, wrist, elbow, or other body part, and with durability as would meet the purpose described herein.

Furthermore, cryotherapy and compression sleeve 10 or sleeve body 20 may include stretchable fabric or liner, such as elastic fabric 50 configured to provide a protective cover around elastic material 40 or fabric liner or insulation between a user's skin and elastic material 40. It is contemplated herein that elastic fabric 50 may be adhered (adhesion) or affixed to one or more surfaces 45, such as first material surface 45 and second material surface 46 wherein elastic fabric 50 may include a protective outer cover, such as first elastic fabric 51 affixed or adhered thereto first material surface 45 and a protective inner or insulating cover, such as second elastic fabric 52 affixed or adhered thereto second material surface 46.

Still furthermore, first material side 41 may include first elastic fabric 51 and second elastic fabric 52 extending therefrom first material side 41 to form first fabric edge 61, wherein first fabric edge 61 may be sealed, affixed, such as sewn 71 together via single or multiple stitch, hemmed, glued, ties, braids, heated, heat pressed, stapled, snapped, hook and loop, taped, or otherwise attached to hold elastic material 40 therein elastic fabric 50. Likewise, second material side 42 may include first elastic fabric 51 and second elastic fabric 52 extending therefrom second material side 42 to form second fabric layer edge 62, wherein second fabric layer edge 62 may be sealed, affixed, such as sewn 72 together via single or multiple stitch, hemmed, glued, ties, braids, heated, heat pressed, stapled, snapped, hook and loop, taped, or otherwise attached to hold elastic material 40 therein elastic fabric 50.

In one embodiment, first fabric edge 61 and second fabric edge 62 may be sealed, affixed, such as sewn 73 together via single or multiple stitch, hemmed, glued, ties, braids, heated, heat pressed, stapled, snapped, hook and loop, taped, or otherwise attached to form multi-directional stretch elastic fabric 50 in combination or integral thereto elastic material 40 as a cylinder, sleeve shaped, or tube, tubular shaped, or open ended tube having diameter 30, or other shape to encompass a body part or section of a limb, such as an ankle, knee, wrist, elbow, or other body part.

Elastic fabric 50 is preferably formed from multi-directional stretch material or compression fabric or other suitable materials such as nylon, synthetic fiber, polymer, Spandex, or the like, that can be utilized, provided such material has sufficient hot/cold absorption and transfer capability and/or multi-directional stretch elastic material capable of being formed as a layer, cylinder, or other shape to encompass a body part or section of a limb, such as an ankle, knee, wrist, elbow, or other body part, and with durability or antimicrobial as would meet the purpose described herein.

Figure 3:
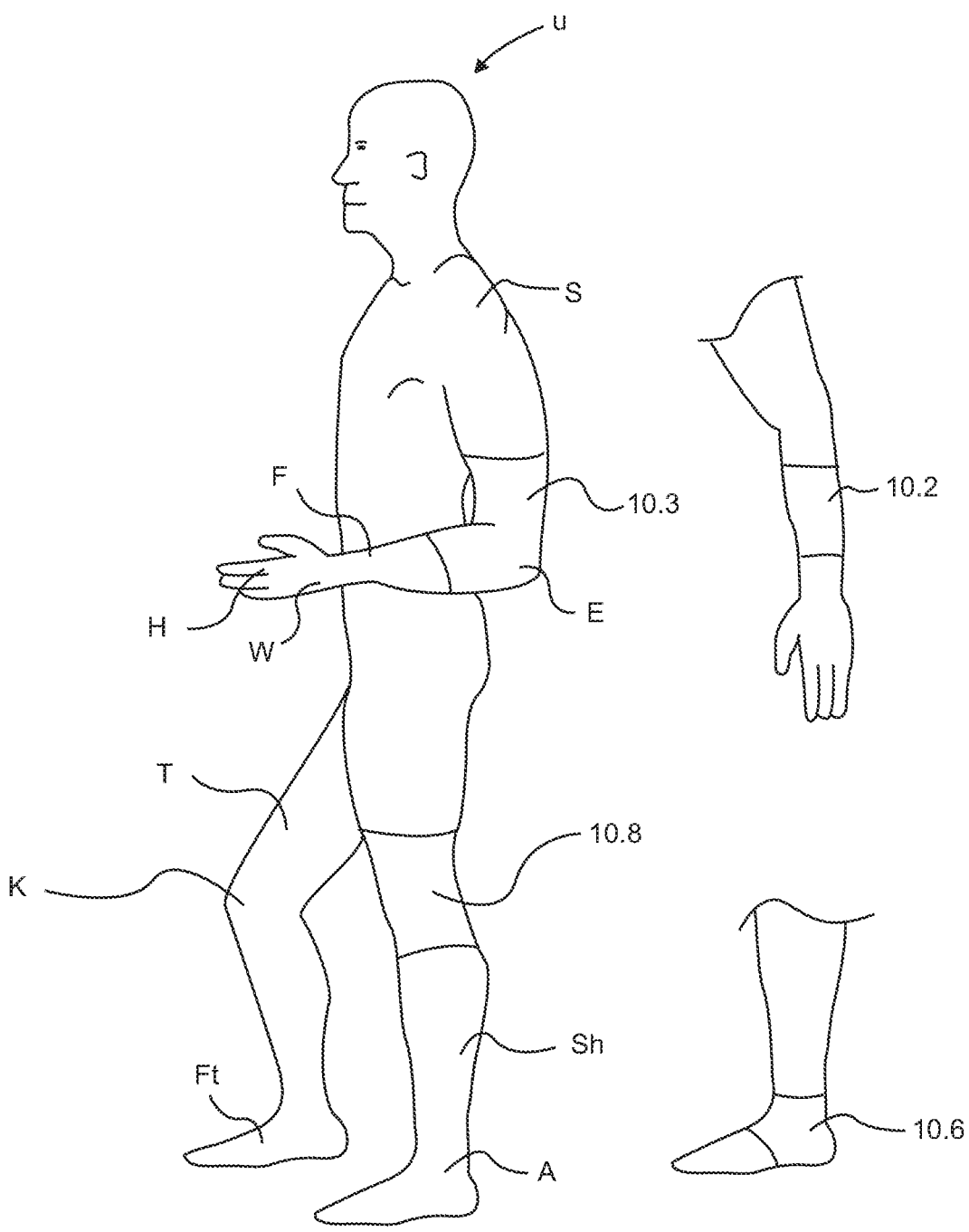
FIG. 3 is a front view of a user shown with a plurality of wearable positions of the exemplary embodiment of the cryotherapy and compression sleeve shown in FIG. 1.

Referring now to FIG. 3 there is illustrated an exemplary embodiment of one or more cryotherapy and compression sleeve 10 positioned thereon a user U. In use, cryotherapy and compression sleeve 10.1 may be fitted or positioned over user U left or right hand H as a hand sleeve, cryotherapy and compression sleeve 10.2 may be fitted or positioned over user U left or right forearm F (hand H, wrist W, and/or forearm F) as an arm sleeve, cryotherapy and compression sleeve 10.3 may be fitted or positioned over user U left or right elbow E as an elbow sleeve, cryotherapy and compression sleeve 10.4 may be fitted or positioned over user U left or right shoulder S as a shoulder sleeve, cryotherapy and compression sleeve 10.5 may be fitted or positioned over user U left or right foot Ft as a foot sleeve, cryotherapy and compression sleeve 10.6 may be fitted or positioned over user U left or right ankle A as an ankle sleeve, cryotherapy and compression sleeve 10.7 may be fitted or positioned over user U left or right shin Sh, cryotherapy and compression sleeve 10.8 may be fitted or positioned over user U left or right knee K as a knee sleeve, cryotherapy and compression sleeve 10.9 may be fitted or positioned over user U left or right thigh T as a thigh sleeve, or fitted or positioned over any other combination of user U body parts or section of a limb, or other body part. To position cryotherapy and compression sleeve 10 thereon user U body parts or section of a limb, or other body part user U must position a hand H or foot Ft therein first sleeve opening 21 and pull first sleeve edge 28 and insert user U body parts or section of a limb therein sleeve body 20 to position sleeve body 20 thereon user U body parts or section of a limb, or other body part user U, and held in place by size of diameter 30 relative to user U and elastic fabric 50 in combination or integral thereto elastic material 40 without use of any attachments, clasps or the like.

Figure 4:
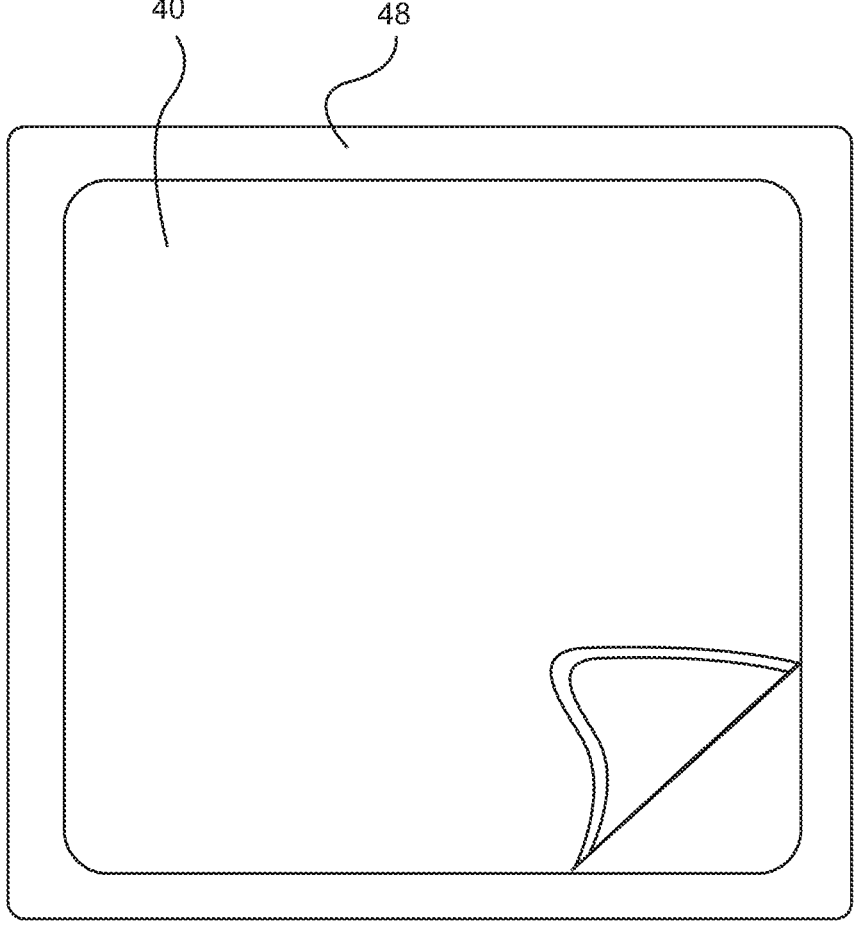
FIG. 4 is a perspective view of a mold tray utilized to form the elastic material of an exemplary embodiment of the cryotherapy and compression sleeve shown in FIG. 1.

Referring now to FIG. 4 there is illustrated an exemplary embodiment of a mold tray utilized to form elastic material 40. Pre elastic material 40 solution or mixture may be poured into a mold or form, such as tray 48 to cure a planar section of one or more elastic material 40. Once cured or predominantly cured may be removed from tray 48 for assembly as cryotherapy and compression sleeve 10.

Figure 5:
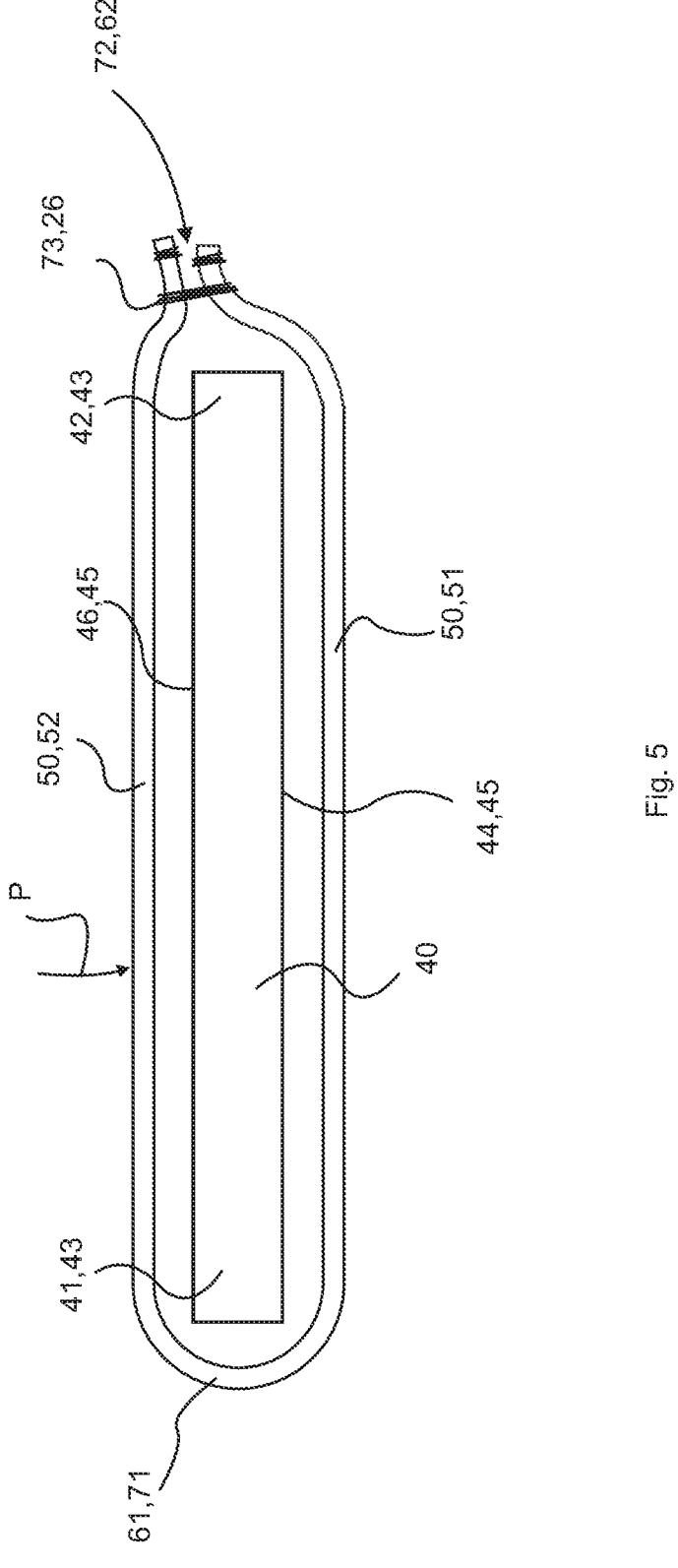
FIG. 5 is a perspective view of the elastic material being affixed to the elastic fabric of cryotherapy and compression sleeve shown in FIG. 1.

Referring now to FIG. 5 there is illustrated an exemplary embodiment of assembly of cryotherapy and compression sleeve 10. Cured, partially, or predominantly cured elastic material 40 may be positioned thereon first section of elastic fabric 50, and more specifically first material surface 44 may be positioned thereon first elastic fabric 51. Next, second section (or folded section shown) of elastic fabric 50 may be positioned thereon elastic material 40, and more specifically second elastic fabric 52 may be positioned thereon second material surface 46. Next, pressure P is applied to compress together second elastic fabric 52, elastic material 40, and first elastic fabric 51 to form the base components of cryotherapy and compression sleeve 10. Preferably, elastic fabric 52, elastic material 40, and first elastic fabric 51 bond, affix, or attach together due to the sticky, tacky, or tackiness of uncured or partially uncured elastic material 40. It is contemplated herein that elastic fabric 52, elastic material 40, and first elastic fabric 51 may bond, affix, or attach together via single or multiple stitch, hemmed, glued, ties, braids, heated, heat pressed, stapled, snapped, hook and loop, taped, or otherwise be attached to configure or shape cryotherapy and compression sleeve 10 or sleeve body 20 in the form of a flat two dimension plane, tube or cylinder. Next first elastic fabric 51 and second elastic fabric 52 may be sewn 71 around perimeter edge 70 via single or multiple stitch, hemmed, glued, ties, braids, heated, heat pressed, stapled, snapped, hook and loop, taped, or otherwise be attached to hold elastic material 40 therein elastic fabric 50. Next first elastic fabric 51 and second elastic fabric 52 may be sewn 72 around perimeter edge 70 via single or multiple stitch, hemmed, glued, ties, braids, heated, heat pressed, stapled, snapped, hook and loop, taped, or otherwise be attached to hold elastic material 40 therein elastic fabric 50.

Next first elastic fabric 51 and second elastic fabric 52 may be sewn 74 around perimeter edge 70 via single or multiple stitch, hemmed, glued, ties, braids, heated, heat pressed, stapled, snapped, hook and loop, taped, or otherwise be attached to hold elastic material 40 therein elastic fabric 50. It is contemplated herein that first elastic fabric 51 and second elastic fabric 52 may be sewn or otherwise attached on one or more or all sides to hold elastic material 40 therein elastic fabric 50.

Referring now to FIG. 6 there is illustrated a flow diagram 600 of a method of making and using cryotherapy and compression sleeve 10 having primary elements of elastic fabric 50 in combination or integral thereto elastic material 40 shown in FIGS. 1-5. In block or step 610, forming a planar or tubular or cylindrical section of one or more elastic material 40 in a mold or form, such as tray 48. In block or step 615A, positioning elastic material 40 thereon elastic fabric 50, and more specifically first material surface 44 may be positioned thereon or affixed thereto first elastic fabric 51. In block or step 615B, positioning elastic fabric 50 thereon or folding thereover elastic material 40 and more specifically first material surface 44 may be positioned thereon or affixed thereto second elastic fabric 52. In block or step 620, pressing P or affixing second elastic fabric 52, elastic material 40, and first elastic fabric 51 together to form the base components of cryotherapy and compression sleeve 10. In block or step 625, affixing or sealing first elastic fabric 51 and second elastic fabric 52 around perimeter edge 70 to hold elastic material 40 therein. In block or step 630, affixing first fabric edge 61 and second fabric edge 62 to form multi-directional stretch elastic fabric 50 in combination or integral thereto elastic material 40 as a cylinder, sleeve shaped, or tube, tubular shape, or open ended tube having diameter 30, or other shape (or cryotherapy and compression sleeve 10) to encompass user's U body part or section of a limb, such as an ankle, knee, wrist, elbow, or other body part. In block or step 635 exposing cryotherapy and compression sleeve 10 to a cold or hot temperature environment, such as freezer or microwave for a duration necessary to bring cryotherapy and compression sleeve 10 to the cold or hot temperature. In block or step 640, positioning or fitting user U body part or section of a limb, or other body part therethrough first sleeve opening 21 and second sleeve opening 22 of cryotherapy and compression sleeve 10. In block or step 645, transferring the hot or cold temperature thereto encompass user's U body part or section of a limb and combination compression of user's U body part or section of a limb.

The foregoing description and drawings comprise illustrative embodiments of the present invention. Having thus described exemplary embodiments, it should be noted by those ordinarily skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one ordinarily skilled in the art to which this invention pertains having the benefit of the teachings presented in the foregoing descriptions and the associated drawings. Although specific terms may be employed herein, they are used in a generic and descriptive sense only and not for purposes of limitation. Moreover, the present invention has been described in detail; it should be understood that various changes, substitutions and alterations can be made thereto without departing from the spirit and scope of the invention as defined by the appended claims. Accordingly, the present invention is not limited to the specific embodiments illustrated herein, but is limited only by the following claims.

What is claimed is:

1. An apparatus for wrapping a body part, said apparatus comprising:

an elastic material, said elastic material having a first surface and a second surface, wherein said elastic material is configured to be exposed to a hot or cold temperature environment and transfer said hot or cold temperature, wherein said elastic material consists of a single, elastic gel material that is configured to stretch in multiple directions;

an elastic fabric part that comprises:

an elastic fabric portion adhered to and covering said first surface of said elastic material;

an elastic fabric portion adhered to and lining said second surface of said elastic material; and wherein said apparatus is configured to provide a compressive force to the body part.

2. The apparatus of claim 1, wherein said elastic fabric part is configured in a sleeve shape with a first sleeve end opening and a second sleeve end opening;

wherein said elastic fabric portion adhered to said first surface is an outer fabric layer portion of said sleeve shape;

wherein said elastic fabric portion adhered to said second surface is an inner fabric layer portion of said sleeve shape;

wherein each of said outer fabric layer portion and said inner fabric layer portion extends between said first sleeve end opening and said second sleeve end opening;

wherein a space is provided between said outer fabric layer portion and said inner fabric layer portion, and said elastic material is located in said space;

wherein said elastic fabric part includes a sewn seam region that joins said outer fabric layer portion and said inner fabric layer portion, and said sewn seam region runs from said first sleeve end opening to said second sleeve end opening.

3. The apparatus of claim 2, wherein said space between said outer fabric layer portion and said inner fabric layer portion includes a first edge running from said first sleeve end opening toward said second sleeve end opening and a second edge running from said first sleeve end opening toward said second sleeve end opening; and wherein said elastic material is configured with a first material side that extends along said first edge of said space and a second material side that extends along said second edge of said space.

4. The apparatus of claim 3, wherein said first material side is separated from said second material side by said sewn seam region.

5. The apparatus of claim 4, wherein said outer fabric layer portion is continuous between a first side of said sewn seam region and a second side of said sewn seam; and wherein said inner fabric layer portion is continuous between said first side of said sewn seam region and said second side of said sewn seam.

6. The apparatus of claim 5, wherein said sleeve shape is tapered.

7. The apparatus of claim 2, wherein said first sleeve end opening's opening diameter is greater than said second sleeve end opening's opening diameter.

8. The apparatus of claim 7, wherein said elastic material is tapered from said first sleeve end opening to said second sleeve end opening and said elastic fabric part is tapered from said first sleeve end opening to said second sleeve end opening.

9. The apparatus of claim 1, wherein said elastic gel material was formed as a layer in a mold or form.

10. An apparatus for wrapping a body part, said apparatus comprising:

an elastic material, said elastic material having a first surface and a second surface, wherein said elastic material is configured to be exposed to a hot or cold temperature environment and transfer said hot or cold temperature, wherein said elastic material is a molded elastic gel material that is formed as a layer with a defined perimeter edge, wherein said layer of said molded elastic gel material is configured to stretch in multiple directions;

an elastic fabric part that comprises:

an elastic fabric portion adjacent to and covering said first surface of said elastic material;

an elastic fabric portion adjacent to and lining said second surf ace-surface of said elastic material; and wherein said apparatus is configured to provide a compressive force to the body part.

11. The apparatus of claim 10, wherein said elastic fabric part is configured in a sleeve shape with a first sleeve end opening and a second sleeve end opening;

wherein said elastic fabric portion adjacent to said first surface is an outer fabric layer portion of said sleeve shape;

wherein said elastic fabric portion adjacent to said second surface is an inner fabric layer portion of said sleeve shape;

wherein each of said outer fabric layer portion and said inner fabric layer portion extends between said first sleeve end opening and said second sleeve end opening;

wherein a space is provided between said outer fabric layer portion and said inner fabric layer portion, and said layer of said molded elastic gel material is located in said space.

12. The apparatus of claim 11, wherein said elastic fabric part includes a sewn seam region that joins said outer fabric layer portion and said inner fabric layer portion, and said sewn seam region runs from said first sleeve end opening to said second sleeve end opening.

13. The apparatus of claim 12, wherein said space between said outer fabric layer portion and said inner fabric layer portion includes a first edge running from said first sleeve end opening toward said second sleeve end opening and a second edge running from said first sleeve end opening toward said second sleeve end opening; and wherein said perimeter edge of said layer of said molded elastic gel material includes a first material side that extends along said first edge of said space and a second material side that extends along said second edge of said space.

14. The apparatus of claim 13, wherein said first material side is separated from said second material side by said sewn seam region.

15. The apparatus of claim 14, wherein said outer fabric layer portion is continuous between a first side of said sewn seam region and a second side of said sewn seam; and wherein said inner fabric layer portion is continuous between said first side of said sewn seam region and said second side of said sewn seam.

16. The apparatus of claim 15, wherein said sleeve shape is tapered.

17. The apparatus of claim 12, wherein said first sleeve end opening's opening diameter is greater than said second sleeve end opening's opening diameter.

18. The apparatus of claim 17, wherein said layer of said molded elastic gel material is tapered from said first sleeve end opening to said second sleeve end opening and said elastic fabric part is tapered from said first sleeve end opening to said second sleeve end opening.

19. An apparatus for wrapping a body part, said apparatus comprising:

an elastic material, said elastic material having a first surface and a second surface, wherein said elastic material is configured to be exposed to a hot or cold temperature environment and transfer said hot or cold temperature, wherein said elastic material is an elastic gel layer that is formed with a defined perimeter edge, wherein said elastic gel layer is configured to stretch in multiple directions;

an elastic fabric part that comprises:

an elastic fabric portion adjacent to and covering said first surface of said elastic material;

an elastic fabric portion adjacent to and lining said second surf ace-surface of said elastic material;

wherein said apparatus is configured to provide a compressive force to the body part.

20. The apparatus of claim 19, wherein said elastic fabric part is configured in a sleeve shape with a first sleeve end opening and a second sleeve end opening;

wherein said elastic fabric portion adjacent to said first surface is an outer fabric layer portion of said sleeve shape;

wherein said elastic fabric portion adjacent to said second surface is an inner fabric layer portion of said sleeve shape;

wherein each of said outer fabric layer portion and said inner fabric layer portion extends between said first sleeve end opening and said second sleeve end opening;

wherein a space is provided between said outer fabric layer portion and said inner fabric layer portion, and said elastic gel layer is located in said space.

21. The apparatus of claim 20, wherein said elastic fabric part includes a sewn seam region that joins said outer fabric layer portion and said inner fabric layer portion, and said sewn seam region runs from said first sleeve end opening to said second sleeve end opening.

22. The apparatus of claim 21, wherein said space between said outer fabric layer portion and said inner fabric layer portion includes a first edge running from said first sleeve end opening toward said second sleeve end opening and a second edge running from said first sleeve end opening toward said second sleeve end opening; and wherein said perimeter edge of said elastic gel layer includes a first material side that extends along said first edge of said space and a second material side that extends along said second edge of said space.

23. The apparatus of claim 22, wherein said first material side is separated from said second material side by said sewn seam region.

24. The apparatus of claim 23, wherein said outer fabric layer portion is continuous between a first side of said sewn seam region and a second side of said sewn seam; and wherein said inner fabric layer portion is continuous between said first side of said sewn seam region and said second side of said sewn seam.

25. The apparatus of claim 20, wherein said first sleeve end opening's opening diameter is greater than said second sleeve end opening's opening diameter.

26. The apparatus of claim 25, wherein said elastic gel layer is tapered from said first sleeve end opening to said second sleeve end opening and said elastic fabric part is tapered from said first sleeve end opening to said second sleeve end opening.

27. The apparatus of claim 20, wherein said sleeve shape is tapered.

\* \* \* \* \*